United States Patent [19]

Hocquaux et al.

[11] Patent Number: 5,543,436
[45] Date of Patent: Aug. 6, 1996

[54] CARBAZOLE DERIVATIVES AND THEIR USE IN COSMETICS

[75] Inventors: Michel Hocquaux, Paris; Michel Philippe, Antony, both of France

[73] Assignee: L'Oreal, Paris, France

[21] Appl. No.: 367,151

[22] PCT Filed: May 10, 1994

[86] PCT No.: PCT/FR94/00549

§ 371 Date: Jan. 10, 1995

§ 102(e) Date: Jan. 10, 1995

[87] PCT Pub. No.: WO94/26711

PCT Pub. Date: Nov. 24, 1994

[30] Foreign Application Priority Data

May 10, 1993 [FR] France ................................. 93 05588

[51] Int. Cl.⁶ ........................... C07D 209/80; A61K 7/00
[52] U.S. Cl. ........................... 424/61; 514/880; 514/881; 514/844; 424/62; 424/63; 424/64; 548/416; 548/418
[58] Field of Search ........................... 548/416, 418, 548/514, 844, 880, 881; 424/61, 62, 63, 64

[56] References Cited

FOREIGN PATENT DOCUMENTS 0562945  9/1993  European Pat. Off. .

OTHER PUBLICATIONS

Napolitano, A. et al. "A Reinvestigation of the Reactions Between 5,6–Dihydroxyindoles and Quinones" Tetrahedron, vol. 43 No. 12, pp. 2749–2754. (1987).

Prasad, "A reinvestigation of the reaction of indole with 1,4–quinones ", Tetrahedron Letters, No. 15, 1974, pp. 1361–1362.

*Primary Examiner*—Jacqueline Haley
*Attorney, Agent, or Firm*—Cushman Darby & Cushman, L.L.P.

[57] ABSTRACT

The present invention relates to novel carbazole derivatives corresponding to the formula:

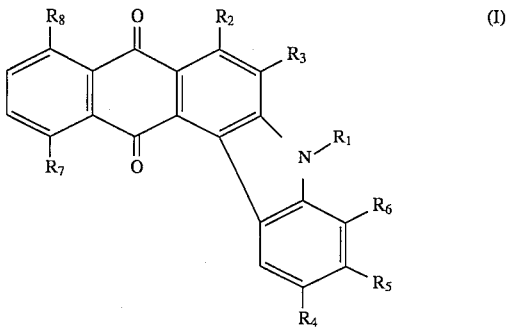

in which $R_1$ is H, benzyl or alkyl; $R_2$ and $R_3$ are a carbethoxy, acetyl, nitrile

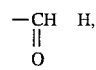

with $R_2=R_3$ other than H, or $R_2$ and $R_3$ form the following ring systems:

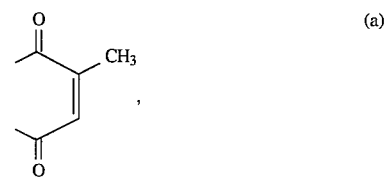

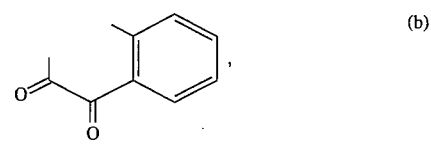

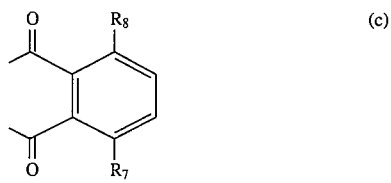

$R_4$ is H, Cl, methoxy, nitrile or nitro; $R_5$, $R_7$ and $R_8$ are H or methoxy; $R_6$ is H or methyl; with the proviso that if $R_2$ and $R_3$ form the ring system (c), at least one of $R_1$, $R_4$, $R_5$, $R_6$, $R_7$ and $R_8$ does not denote H.

The invention also relates to the use in cosmetics of these novel compounds as pigments, and in particular in cosmetic compositions intended for the treatment and/or the coloration of keratinous substances.

22 Claims, No Drawings

CARBAZOLE DERIVATIVES AND THEIR USE IN COSMETICS

This application is a National Stage Application of PCT/FR94/00549 filed May 10, 1994 and published as WO94/26711 on Nov. 24, 1994.

The present invention relates to novel carbazole derivatives and to a process for their preparation, as well as to their use in cosmetics, the cosmetic compositions containing them and the cosmetic treatment processes using them.

In the cosmetics field, and in particular for make-up compositions such as foundation compositions, tinted creams, mascaras, blushers and eye shadows, lipsticks and nail varnishes, pigments are being sought which are capable of imparting to these various types of products a varied palette of colorations which are reproducible over time and are insoluble in most of the cosmetic media used such as water and cosmetically acceptable solvents. These pigments should, moreover, be stable at the pHs usually used or encountered in the cosmetics field.

Carbazole derivatives are known in the state of the art, these being products of addition of indole compounds with quinones, such as the product of addition of 1,4-naphthoquinone with 1-methyl-5,6-dihydroxyindole, which leads to 2,3-dihydroxy-5-methyldinaphtho-[2,3-a:2',3'-c]carbazole-6,11,12,17-tetrone described in the articles from PROTA (Tetrahedron Letters, Vol. 43, No. 12 pages 2749–54, 1987 and Gazetta Chemica Italiana, 119, 1989), or alternatively the product of addition of 1,4-naphthoquinone with indole, which leads to 5-H-dinaphtho[2,3-a:2', 3'-c]carbazole- 6,11, 12,17-tetrone described in the article from PROTA (Gazetta Chemica Italiana, 119, 1989) and in the article from PRASAD (Tetrahedron letters, No. 15, pages 1361–1362, 1974).

The Applicant has just discovered novel carbazole derivatives whose use as pigments is particularly advantageous in the cosmetics field, and in particular their use in make-up compositions, especially foundations, tinted creams, mascaras, blushers and eye shadows, lipsticks, nail varnishes and nonpermanent dyeing compositions for the hair. These pigments enable a very varied palette of colorations, which are very much sought after in the cosmetics field and are reproducible, to be obtained, ranging from yellow to brown and including orange-yellow, orange and bright red. In addition, they are stable at pHs between 6 and 8 and are insoluble in most cosmetic media.

In addition, the high crystallinity of these pigments prevents the phenomenon of the colors separating out in the formulations.

One subject of the invention consists of novel carbazole derivatives and the synthesis thereof.

The subject of the invention is also the use of these pigments in cosmetic compositions.

Another subject of the invention consists of the cosmetic compositions containing this pigment, as well as their application for the cosmetic treatment and/or the coloration of keratinous substances such as the skin, the nails the eyelashes, the eyebrows and the hair.

Other subjects of the invention will become apparent on reading the description and the examples which follow.

The novel compounds in accordance with the present invention correspond to the formula (I)

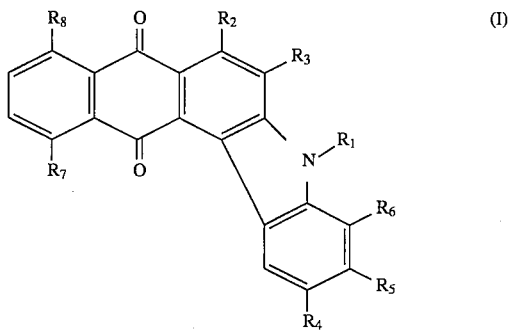

in which,
- $R_1$ represents a hydrogen atom, a benzyl radical, or a $C_1$–$C_{16}$ alkyl radical which may or may not be branched and may or may not be saturated;
- $R_2$ and $R_3$ denote, independently of each other, the carbethoxy, acetyl, nitrile or

radical, or a hydrogen atom, it not being possible, however, for $R_2$ and $R_3$ simultaneously to represent a hydrogen atom, or $R_2$ and $R_3$ form the following ring systems:

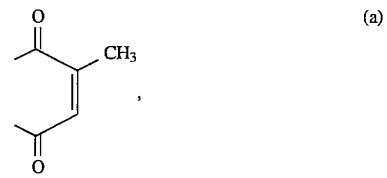

(a)

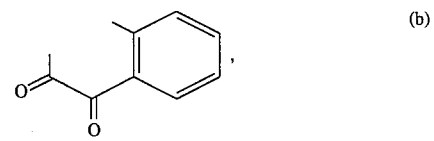

(b)

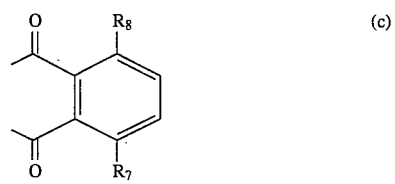

(c)

- $R_4$ represents a hydrogen atom, the methoxy, nitrile or nitro radical or a chlorine atom;
- $R_5$, $R_7$ and $R_8$ represent, independently of each other, a hydrogen atom or the methoxy radical;
- $R_6$ represents a hydrogen atom or the methyl radical;

with the proviso that if $R_2$ and $R_3$ form the ring system (c), at least one of $R_1$, $R_4$, $R_5$, $R_6$, $R_7$ and $R_8$ does not denote a hydrogen atom.

The particularly preferred compounds are chosen from:
2,3-dimethoxy-5-H-dinaphtho[2,3-a:2',3'-c]carbazole- 6,11, 12,17-tetrone,
10,13-dimethoxy-5H-dinaphtho[2,3-a:2',3'-c]carbazole-6, 11,12,17-tetrone,
7,16-dimethoxy-5H-dinaphtho[2,3-a:2',3'-c]carbazole- 6,11, 12,17-tetrone,
7,13-dimethoxy-5H-dinaphtho[2,3-a:2',3'-c]carbazole- 6,11, 12,17-tetrone, 10,16-dimethoxy-5H-dinaphtho[2,3-a:2',3' -c]carbazole-6,11,12,17-tetrone, 2-methoxy-5H-dinaphtho[2,3-a:2',3' -c]carbazole- 6,11,12,17-tetrone, 4-methyl-5H-dinaphtho[2,3-a:2',3'-c]carbazole- 6,11,12,17-tetrone, 2-chloro-5H-dinaphtho[2,3-a:2',3'-c]carbazole- 6,11,12,17-tetrone, 7-methyl-5-hexadecylnaphtho[2,3-a]benzo[2',3'-c]carbazole-6,9,10,15-tetrone, 5-hexadecyldinaphtho[2,3-a:2',3'-c]carbazole- 6,11,12,17-tetrone, 2-cyano-5H-dinaphtho [2,3 -a:2',3'-c]carbazole- 6,11,12,17-tetrone, 2 -nitro-10,13-dimethoxy-5H-dinaphtho[2,3-a:2',3'-c] carbazole-6,11,12,17-tetrone, 2-nitro-7,16-dimethoxy-5H-dinaphtho[2,3-a:2',3'-c]carbazole-6,11,12,17-tetrone, 2-nitro-7,13-dimethoxy-5H-dinaphtho[2,3-a:2',3'-c] carbazole-6,11,12,17-tetrone, 2-nitro-10,16-dimethoxy-5H-dinaphtho[2,3-a:2',3'-c]carbazole-6,11,12,17-tetrone.

The compounds of formula (I) in accordance with the present invention may be obtained by two different preparation processes.

1) The compounds of formula (I) in which $R_2$ and $R_3$ form the ring system (c) may be prepared in the following way:
a 1,4-naphthoquinone of formula (II)

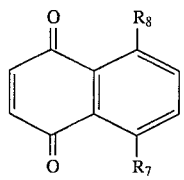

(II)

in which $R_7$ and $R_8$ represent, independently of each other, either a hydrogen atom or the methoxy radical, is reacted in an acidic medium with an indole compound of formula (III)

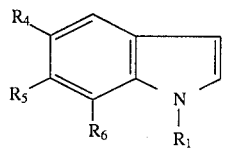

(III)

in which
$R_1$ represents a hydrogen atom, a benzyl radical or a $C_1$–$C_{16}$ alkyl radical which may or not be branched and may or may not be saturated;

$R_4$ represents a hydrogen atom, the methoxy, nitrile or nitro radical or a chlorine atom;

$R_5$ denotes a hydrogen atom or the methoxy radical, $R_6$ denotes a hydrogen atom or the methyl radical, with the proviso that if $R_7$ and $R_8$ each denote a hydrogen atom, at least one of $R_1$, $R_4$, $R_5$ and $R_6$ is other than a hydrogen atom.

Addition of the 1,4-naphthoquinone to position 2 or 3 of the indole compound is followed by a cyclization, in order to obtain the carbazole derivative of formula (I) in which $R_2$ and $R_3$ form the ring system (c).

The acidic reaction medium preferably consists of glacial acetic acid or of aqueous acetic acid. The process is generally performed at room temperature or at the reflux temperature of acetic acid.

2) The compounds of formula (I) may be prepared by a second process.

a) In a first step, a 1,4-naphthoquinone of formula (II):

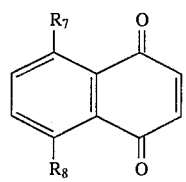

(II)

in which $R_7$ and $R_8$, independently of each other, represent a hydrogen atom or the methoxy radial, is reacted in an acidic medium with an indole compound of formula (III):

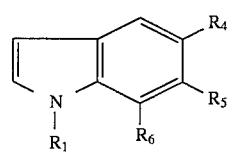

(III)

in which,
$R_1$ represents a hydrogen atom, a benzyl radical or a $C_1$–C16 alkyl radical which may or may not be branched and may or may not be saturated;

$R_4$ represents a hydrogen atom, the nitrile, methoxy or nitro radical or a chlorine atom;

$R_5$ represents a hydrogen atom or the methoxy radical;

$R_6$ represents a hydrogen atom or the methyl radical;

the reaction medium used preferably consists of glacial acetic acid, aqueous acetic acid or ethanol with a few drops of hydrochloric acid, according to BULOK & MASON (J. Chem. Soc. 1951, 703). The process is generally performed at room temperature or at the reflux temperature of acetic acid.

The indolyl-1,4-naphthoquinone compound of formula (IV) is obtained:

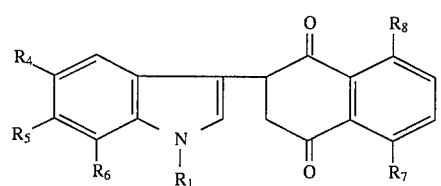

(IV)

in which $R_1$, $R_4$, $R_6$, $R_7$ and $R_8$ have the same meanings as indicated above.

b) This indolyl-1,4-naphthoquinone compound of formula (IV) is reacted, in an acidic reaction medium preferably consisting of glacial acetic acid or of aqueous acetic acid, with a dienophile chosen from:

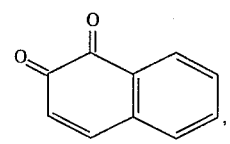

(V)

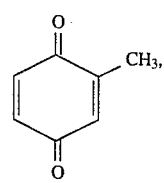

(VI)

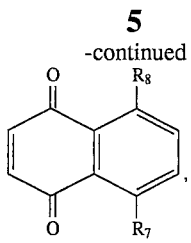 (VII)

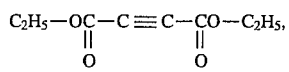 (VIII)

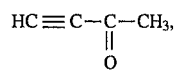 (IX)

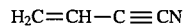 (X)

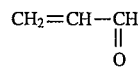 (XI)

with $R_7$ and $R_8$ having the same meanings as indicated above;

with the proviso that if the indolyl-1,4-naphthoquinone compound of formula (IV) is reacted with the dienophile of formula (VII), $R_1$, $R_4$, $R_5$, $R_6$, $R_7$ and $R_8$ cannot simultaneously denote a hydrogen atom.

Another subject of the invention is the use of this compound of formula (I) as a pigment in cosmetic compositions for the treatment and/or dyeing of keratinous substances such as the skin, the nails and the hair. Given the insoluble nature of this pigment, it is used more particularly in foundation compositions, tinted creams, mascaras, blushers and eye shadows, lipsticks, nail varnishes and nonpermanent dyeing compositions for the hair. It may be used alone or as a mixture with other conventional inorganic or organic pigments.

The cosmetic compositions which constitute another subject of the invention are characterized in that they contain at least one compound corresponding to the formula (I) defined above in a cosmetically acceptable medium.

The pigment of formula (I) is generally used at a concentration which may range between 0.1 and 80% by weight, and preferably between I and 30% by weight, relative to the total weight of the composition.

The cosmetically acceptable medium is a medium which is essentially not a solvent for the pigment.

The term medium which is essentially not a solvent refers to a medium which dissolves less than 1% of the said pigment.

The compositions may take the form of a lotion, a thickened lotion, a gel, emulsions (creams, milks or ointments), vesicle dispersions, a powder or a stick. They may optionally be packaged as an aerosol and may take the form of a foam or a spray.

Compositions are preferably emulsions of the oil-in-water type or water-in-oil type or are liposomal dispersions or alternatively solid preparations.

When they are used in the form of emulsions, they may additionally contain surface-active agents which are well known in the state of the art, such as anionic, nonionic, cationic or amphoteric surface-active agents or mixtures thereof.

These compositions may also contain fatty substances, organic solvents, silicones, thickening agents, softening agents, sunscreen agents, anti-free-radical agents, anti-foaming agents, moisturizing agents, fragrances, preserving agents, antioxidants, fillers, sequestering agents, treatment agents such as nonionic, cationic, anionic or amphoteric polymers or mixtures thereof, propellants, and basifying or acidifying agents.

The fatty substances may consist of an oil or a wax or mixtures thereof, fatty acids, fatty alcohols, fatty acid esters, vaseline, paraffin, lanolin, hydrogenated lanolin or acetylated lanolin.

The oils are chosen from animal oils, vegetable oils, mineral oils or synthetic oils and especially hydrogenated palm oil, hydrogenated castor oil, liquid paraffin, paraffin oil, purcellin oil and silicone oils.

The waxes are chosen from animal waxes, fossil waxes, vegetable waxes, mineral waxes or synthetic waxes. Beeswaxes, carnauba wax, candelilla wax, sugar cane wax, Japan wax, ozokerites, montan wax, microcrystalline waxes and paraffin waxes may more particularly be mentioned.

When the compositions are used for coloring the nails, they take the form of so-called "nail varnish" products containing the pigment in accordance with the invention in dispersed form in a cosmetically acceptable solvent containing one or more resins and ingredients usually used in products of this type.

When the compositions are used for dyeing the hair, they preferably comprise a medium which is suitable for nonpermanent dyeing, consisting of water, a solvent or a mixture of water and one or more cosmetically acceptable solvent(s), containing at least one pigment in accordance with the invention in dispersed form.

The solvents are chosen more particularly from $C_1$–$C_6$ lower alcohols, alkylene glycols such as ethylene glycol or propylene glycol, glycol ethers such as the ethylene glycol monomethyl, monoethyl or monobutyl ethers, ethylene glycol monoethyl ether acetate, the propylene glycol and dipropylene glycol monomethyl ethers, and methyl lactate.

The solvents particularly preferred are ethyl alcohol and propylene glycol.

The compositions in accordance with the invention may also contain, in addition to the pigment defined above, other pigments which are generally used in cosmetics, especially white or colored pigments and pearlescent and/or nacreous pigments which allow the colorations to be varied or alternatively which allow the protection towards ultraviolet radiation to be increased. Among these pigments, there may be used nanopigments of metal oxides such as titanium oxide, zinc oxide, cerium oxide and/or zirconium oxide, these nanopigments having a mean diameter of less than 100 nm, preferably between 1 and 50 nm. These pigments may be coated.

Another subject of the invention consists of a process for the coloration or the make-up of keratinous substances such as the skin, the nails, the eyelashes, the eyebrows and the hair, using a composition containing at least one pigment corresponding to the formula (I) as defined above, in a cosmetically acceptable medium.

The examples which follow are intended to illustrate the invention without, however, being of a limiting nature.

PREPARATION EXAMPLES

The compounds of formula (I) may be obtained by two preparation processes.

Preparation process A

A mixture of 6.5 mmol of 1,4-naphthoquinone which is optionally substituted, corresponding to the formula (II), 3 mmol of an indole compound of formula (III) and from 10 to 30 ml of acetic acid is stirred at a temperature between 45° and 90° C. for 6 to 48 hours in a three-necked flask fitted with a thermometer, a condenser and a magnetic stirrer. The mixture is then allowed to return to room temperature.

The reaction mixture is filtered and the precipitate obtained is then washed with water, with ethanol and optionally with acetone.

The yields are between 15% and 50%.

Preparation process B

A mixture of 5 mmol of 1,4-monoindolylnaphthoquinone of formula (IV), 3 mmol of a dienophile corresponding to one of the formulae (V) to (XI) and from 15 to 30 ml of acetic acid is stirred at a temperature between 45° and 90° C. for 6 to 48 hours in a three-necked flask fitted with a thermometer, a condenser and a magnetic stirrer. The mixture is then allowed to return to room temperature.

The reaction mixture is filtered and the precipitate obtained is then washed with water, with ethanol and optionally with acetone.

Chromatography on a column of silica gel is optionally carried out.

The yields are between 10 and 50%.

Example 1

Preparation of 2,3-dimethoxy-5H-dinaphtho[2,3-a:2',3'-c]carbazole-6,11,12,17-tetrone This compound is prepared according to preparation process A. A brown-colored product is obtained, having the following characteristics:

Melting point: >350° C.

Elemental analysis:

|  | C % | H % | N % | O % |
|---|---|---|---|---|
| Theoretical | 73.85 | 3.49 | 2.87 | 19.69 |
| Found | 73.41 | 3.99 | 2.66 | 19.75 |

Example 2

Preparation of the mixture:
- 10,13-dimethoxy-5H-dinaphtho[2,3-a:2',3'-c]carbazole-6,11,12,17-tetrone,
- 7,16-dimethoxy-5H-dinaphtho[2,3-a:2',3'-c]carbazole-6,11,12,17-tetrone,
- 7,13-dimethoxy-5H-dinaphtho[2,3-a:2',3'-c]carbazole-6,11,12,17-tetrone,
- 10,16-dimethoxy-5H-dinaphtho[2,3-a:2',3'-c]carbazole-6,11,12,17-tetrone.

This mixture is obtained by implementation of preparation process A. An orange-colored product is obtained, which has the following characteristics:

Melting point: >260° C.

Elemental analysis:

|  | C % | H % | N % | O % |
|---|---|---|---|---|
| Theoretical | 73.85 | 3.49 | 2.87 | 19.69 |
| Found | 73.51 | 3.90 | 2.68 | 19.52 |

Example 3

Preparation of 2-methoxy-5H-dinaphtho[2,3-a:2',3'-c]carbazole-6,11,12,17-tetrone This compound is obtained by implementation of preparation process A. A brown product is obtained, having the following characteristics:

Melting point: >260° C.

Elemental analysis:

|  | C % | H % | N % | O % |
|---|---|---|---|---|
| Theoretical | 76.15 | 3.31 | 3.06 | 17.49 |
| Found | 75.94 | 3.28 | 2.90 | 17.39 |

Example 4

Preparation of 4-methyl-5H-dinaphtho[2,3-a:2',3'-c]carbazole-6,11,12,17-tetrone

This compound is obtained by implementation of preparation process A. A red-colored product is obtained, having the following characteristics:

Melting point: >260° C.

Elemental analysis:

|  | C % | H % | N % | O % |
|---|---|---|---|---|
| Theoretical | 78.90 | 3.42 | 3.17 | 14.50 |
| Found | 79.15 | 3.36 | 2.98 | 14.34 |

Example 5

Preparation of 2-chloro-5H-dinaphtho[2,3-a:2',3'-c]carbazole-6,11,12,17-tetrone

This compound is obtained by implementation of preparation process A. An orange-colored product is obtained, having the following characteristics:

Melting point: >260° C.

Elemental analysis:

|  | C % | H % | N % | O % |
|---|---|---|---|---|
| Theoretical | 72.82 | 2.62 | 3.03 | 13.86 |
| Found | 72.30 | 2.63 | 2.91 | 13.94 |

Example 6

Preparation of 7-methyl-5-hexadecylnaphtho[2,3-a]benzo[2',3'-c]carbazole-6,9,10,15-tetrone This compound is obtained by implementation of preparation process B. After chromatography on silica gel using chloroform as eluent, a red-colored product crystallized with 0.5 $H_2O$ is obtained, having the following characteristics:

Melting point: 130°–132° C.

Elemental analysis:

|  | C % | H % | N % | O % |
|---|---|---|---|---|
| Theoretical | 78.79 | 7.44 | 2.24 | 11.52 |
| Found | 78.13 | 7.25 | 2.35 | 10.70 |

Example 7

Preparation of 5-hexadecyldinaphtho[2,3-a:2',3'-c] carbazole-6,11,12,17-tetrone

This compound is obtained by implementation of preparation process A. An orange-colored product crystallized with 0.5 $H_2O$ is obtained, having the following characteristics:

Melting point: 124°–125° C.

Elemental analysis:

|  | C % | H % | N % | O % |
|---|---|---|---|---|
| Theoretical | 81.07 | 6.96 | 2.15 | 9.82 |
| Found | 80.77 | 7.00 | 2.24 | 9.93 |

Example 8

Preparation of 2-cyano-5H-dinaphtho[2,3-a:2',3'-c] carbazole-6,11,12,17-tetrone

This compound is obtained by implementation of preparation process A. A brown-colored product crystallized with 0.33 $H_2O$ is obtained, having the following characteristics:

Melting point: >260° C.

Elemental analysis:

|  | C % | H % | N % | O % |
|---|---|---|---|---|
| Theoretical | 75.91 | 2.76 | 6.10 | 15.11 |
| Found | 75.97 | 2.64 | 6.04 | 15.44 |

Example 9

Preparation of the mixture of 2-nitro-10,13-dimethoxy-5H-dinaphtho[2,3-a:2',3'-c] carbazole-6,11,12,17-tetrone 2-nitro-7,16-dimethoxy-5H-dinaphtho[2,3-a:2',3' -c]carbazole- 6,11,12,17-tetrone 2-nitro-7,13-dimethoxy-5H-dinaphtho[2,3-a:2',3'-c]carbazole- 6,11,12,17-tetrone and 2-nitro-10,16-dimethoxy-5H-dinaphtho[2,3-a:2',3'- c]carbazole-6,11,12,17-tetrone This mixture is obtained by implementation of preparation process A. An orange-colored product crystallized with 1 mol of water is obtained, having the following characteristics:

Melting point: >260° C.

Elemental analysis:

|  | C % | H % | N % | O % |
|---|---|---|---|---|
| Theoretical | 65.45 | 3.29 | 5.08 | 26.15 |
| Found | 64.75 | 3.29 | 5.40 | 25.02 |

Examples of Formulations

| Face powder: | |
|---|---|
| Talc | 100 g |
| Polyethylene powder | 5.00 g |
| Magnesium carbonate | 11.00 g |
| Isopropyl myristate | 1.50 g |
| Liquid petrolatum | 1.50 g |
| Sorbitol | 0.50 g |
| Mixture of compounds of Example 9 | 0.25 g |
| Insoluble pigment consisting of a dye from the indigo family deposited on a filler, known as DC Red 30 LAKE in the CTFA dictionary | 0.65 g |
| Ultramarine blue | 0.15 g |
| Titanium mica | 5.00 g |

| Lipstick | |
|---|---|
| Castor oil | 100 g |
| Butylhydroxytoluene (BHT) | 0.15 g |
| Liquid lanolin | 15.00 g |
| Microcrystalline wax | 15.00 g |
| Sesame oil | 11.00 g |
| 1-[[4-(Phenylazo)phenyl]azo]-2-naphthalenol, known as DC Red No. 17 in the CTFA dictionary | 1.00 g |
| Compound of Example 8 | 1.00 g |
| Compound of Example 5 | 2.00 g |
| Titanium mica | 5.00 g |
| Octyl glycerol behenate | 15.00 g |
| Fragrance | q.s |

| Nail varnish | |
|---|---|
| Toluene | 100 g |
| Nitrocellulose | 10.90 g |
| Toluenesulfonamide formaldehyde resin | 9.85 g |
| Acetyltributyl citrate | 6.50 g |
| Butyl acetate | 21.80 g |
| Ethyl acetate | 9.40 g |
| Stearalkonium hectorite | 1.36 g |
| Citric acid | 0.06 g |
| Ultramarine blue | 0.01 g |
| Titanium dioxide | 0.77 g |
| Calcium salt of 3-hydroxy-4-[(l-sulfo-2-naphthalenyl)azo]-2-naphthalenecarboxylic acid, known as DC Red 34 in the CTFA dictionary | 0.07 g |
| Compound of Example 5 | 0.50 g |
| Titanium mica | 0.60 g |
| Isopropyl alcohol | 7.80 g |

We claim:

1. A compound corresponding to the formula:

in which, $R_1$ represents a hydrogen atom, a benzyl radical, or a $C_1$–$C_{16}$ alkyl radical which may or may not be branched and may or may not be saturated;

$R_2$ and $R_3$ denote, independently of each other, a carbethoxy, acetyl, nitrile or $$-\overset{\text{O}}{\underset{\|}{\text{C}}}\text{H}$$

radical, or a hydrogen atom, or $R_2$ and $R_3$ are selected from the group consisting of

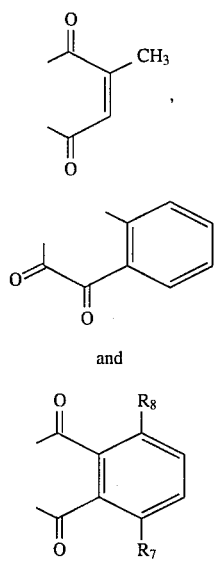

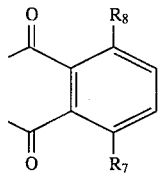

$R_4$ represents a hydrogen atom, a methoxy, nitrile or nitro radical or a chlorine atom;

$R_5$, $R_7$ and $R_8$ represent, independently of each other, a hydrogen atom or a methoxy radical;

$R_6$ represents a hydrogen atom or a methyl radical; with the provisos that if $R_2$ and $R_3$ form the ring system (c), at least one of $R_1$, $R_4$, $R_5$, $R_6$, $R_7$ and $R_8$ does not denote a hydrogen atom and $R_2$ and $R_3$ are not simultaneously a hydrogen atom.

2. The compound according to claim 1 selected from the group consisting of 2,3-dimethoxy-5-H-dinaphtho[2,3-a:2',3'-c]carbazole-6,11,12,17-tetrone;

10,13-dimethoxy-5H-dinaphtho[2,3-a:2',3'-c]carbazole-6,11,12,17-tetrone;

7,16-dimethoxy-5H-dinaphtho[2,3-a:2',3'-c]carbazole-6,11,12,17-tetrone;

7,13-dimethoxy-5H-dinaphtho[2,3-a:2',3'-c]carbazole-6,11,12,17-tetrone;

10,16-dimethoxy-5H-dinaphtho[2,3-a:2',3'-c]carbazole-6,11,12,17-tetrone;

2-methoxy-5H-dinaphtho[2,3-a:2',3'-c]carbazole- 6,11,12,17-tetrone;

4-methyl-5H-dinaphtho[2,3-a:2',3'-c]carbazole-6,11,12, 17tetrone;

2-chloro-5H-dinaphtho[2,3-a:2',3'-c]carbazole- 6,11,12, 17tetrone;

7-methyl-5-hexadecylnaphtho[2,3-a]benzo[2',3'-c]carbazole- 6,9,10,15-tetrone;

5-hexadecyldinaphtho[2,3-a:2',3'-c]carbazole- 6,11,12, 17tetrone;

2-cyano-5H-dinaphtho[2,3-a:2',3'-c]carbazole- 6,11,12, 17tetrone;

2-nitro-10,13-dimethoxy-5H-dinaphtho-[2,3-a:2',3'-c] carbazole-6,11,12,17-tetrone;

2-nitro-7,16-dimethoxy-5H-dinaphtho-[2,3-a:2',3'-c]carbazole-6,11,12,17-tetrone;

2-nitro-7,13-dimethoxy-5H-dinaphtho-[2,3-a:2',3'-c]carbazole-6,11,12,17-tetrone; and 2-nitro-10,16-dimethoxy-5H-dinaphtho-[2,3-a:2',3'-c] carbazole-6,11,12,17-tetrone.

3. A method of cosmetic treatment comprising applying a cosmetic composition to at least one of the skin, nails or hair; said cosmetic composition comprising a compound corresponding to the formula:

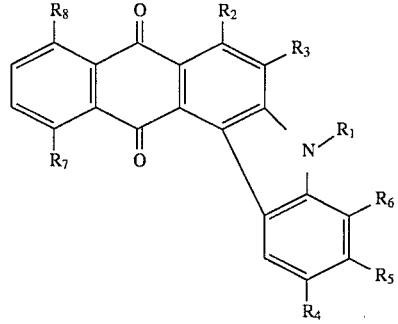

in which, $R_1$ represents a hydrogen atom, a benzyl radical, or a $C_1$–$C_{16}$ alkyl radical which may or may not be branched and may or may not be saturated;

$R_2$ and $R_3$ denote, independently of each other, a carbethoxy, acetyl, nitrile or

radical, or a hydrogen atom, or $R_2$ and $R_3$ are selected from the group consisting of

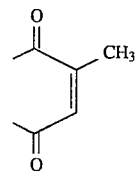

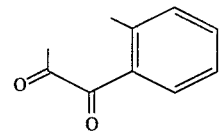

and

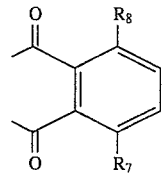

$R_4$ represents a hydrogen atom, a methoxy, nitrile or nitro radical or a chlorine atom;

$R_5$, $R_7$ and $R_8$ represent, independently of each other, a hydrogen atom or a methoxy radical;

$R_6$ represents a hydrogen atom or a methyl radical; with the provisos that if $R_2$ and $R_3$ form the ring system (c), at least one of $R_1$, $R_4$, $R_5$, $R_6$, $R_7$ and $R_8$ does not denote a hydrogen atom and $R_2$ and $R_3$ are not simultaneously a hydrogen atom.

4. The method according to claim 3 wherein the cosmetic composition is in the form of at least one of a foundation compositions, tinted cream, mascara, eye shadow, lipstick, nail varnish or nonpermanent dyeing composition for the hair.

5. A cosmetic composition intended for the cosmetic treatment or for the coloration of keratinous substances, comprising, in a cosmetically acceptable medium, at least one pigment consisting of the compound corresponding to the formula:

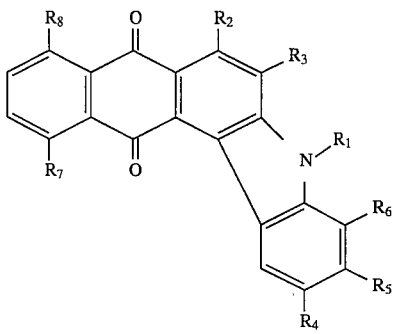

in which,

R$_1$ represents a hydrogen atom, a benzyl radical, or a C$_1$–C$_{16}$ alkyl radical which may or may not be branched and may or may not be saturated;

R$_2$ and R$_3$ denote, independently of each other, a carbethoxy, acetyl, nitrile or

radical, or a hydrogen atom, or R$_2$ and R$_3$ are selected from the group consisting of

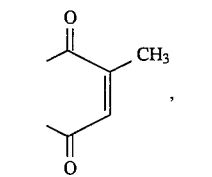 (a)

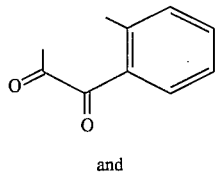 (b)

and

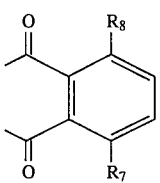 (c)

R$_4$ represents a hydrogen atom, a methoxy, nitrile or nitro radical or a chlorine atom;

R$_5$, R$_7$ and R$_8$ represent, independently of each other, a hydrogen atom or a methoxy radical;

R$_6$ represents a hydrogen atom or a methyl radical; with the provisos that if R$_2$ and R$_3$ form the ring system (c), at least one of R$_1$, R$_4$, R$_5$, R$_6$, R$_7$ and R$_8$ does not denote a hydrogen atom and R$_2$ and R$_3$ are not simultaneously a hydrogen atom.

6. The composition according to claim 5 wherein the pigment of formula (I) is present at a concentration of between 0.1 and 80% by weight relative to the total weight of the composition.

7. The composition according to claim 5 wherein the pigment of formula (I) is present at a concentration of between 1 and 30% by weight relative to the total weight of the composition.

8. The composition according to claim 6 in the form of a lotion, a thickened lotion, a gel, an emulsion, a vesicle dispersion, a powder or a stick.

9. The composition according to claim 7 in the form of a lotion, a thickened lotion, a gel, an emulsion, a vesicle dispersion, a powder or a stick.

10. The composition according to claim 6 packaged as an aerosol in the form of a spray or foam.

11. The composition according to claim 7 packaged as an aerosol in the form of a spray or foam.

12. The composition according to claim 5 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

13. The composition according to claim 6 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

14. The composition according to claim 7 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

15. The composition according to claim 8 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

16. The composition according to claim 9 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

17. The composition according to claim 10 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

18. The composition according to claim 11 further comprising fatty substances, organic solvents, silicones, thickening agents, softening agents, surfactants, sunscreen agents, antifree-radical agents, antifoaming agents, moisturizing agents, fragrances, preserving agents, antioxidants, fillers, sequestering agents, treatment agents, propellants, basifying agents or acidifying agents, or other pigments.

19. The composition according to claim 5 in the form of a dispersion of the pigment in a cosmetically acceptable nail coloring solvent containing one or more resins.

20. A method of coloring nails comprising applying to nails the composition according to claim 19.

21. The composition according to claim 5 in the form of a dispersion of the pigment in a medium which is suitable for dyeing of keratinous fibers.

22. A method of dyeing of keratinous fibers comprising applying to said hair the composition according to claim 21.

* * * * *